US008728500B2

(12) United States Patent
McDermott et al.

(10) Patent No.: US 8,728,500 B2
(45) Date of Patent: May 20, 2014

(54) COMPOSITION CONTAINING A POLYORGANOSILOXANE POLYMER, A THICKENING AGENT AND AT LEAST ONE VOLATILE ALCOHOL

(75) Inventors: Padraig McDermott, Meudon (FR); Michell Chen, Edison, NJ (US); Yoriko Kawaratani, Cranford, NJ (US); Philippe Ilekti, Maisons-Alfort (FR); Florence Levy, Paris (FR); Xavier Blin, Paris (FR)

(73) Assignee: L'Oreal, Paris (FR)

( * ) Notice: Subject to any disclaimer, the term of this patent is extended or adjusted under 35 U.S.C. 154(b) by 396 days.

(21) Appl. No.: 12/949,976

(22) Filed: Nov. 19, 2010

(65) Prior Publication Data
US 2011/0129431 A1 Jun. 2, 2011

Related U.S. Application Data

(63) Continuation-in-part of application No. 11/967,414, filed on Dec. 31, 2007, now abandoned, which is a continuation-in-part of application No. 10/538,924, filed as application No. PCT/EP03/15006 on Dec. 8, 2003, now Pat. No. 7,887,786.

(60) Provisional application No. 60/438,782, filed on Jan. 9, 2003, provisional application No. 60/882,697, filed on Dec. 29, 2006.

(30) Foreign Application Priority Data

Dec. 17, 2002 (FR) ..................................... 02 16040

(51) Int. Cl.
*A61Q 1/02* (2006.01)
*A61Q 1/06* (2006.01)
*A61K 8/92* (2006.01)
*A61K 8/898* (2006.01)

(52) U.S. Cl.
USPC ............. 424/401; 424/64; 424/63; 424/78.03

(58) Field of Classification Search
USPC ........................................................ 424/401
See application file for complete search history.

(56) References Cited

U.S. PATENT DOCUMENTS

| 2,823,195 | A | | 2/1958 | Shorr et al. |
| 2,823,218 | A | | 2/1958 | Speier et al. |
| 3,723,566 | A | | 3/1973 | Thompson et al. |
| 4,137,306 | A | * | 1/1979 | Rubino et al. ................. 424/68 |
| 4,322,400 | A | | 3/1982 | Yuhas |
| 4,822,852 | A | | 4/1989 | Wittman et al. |
| 5,262,505 | A | | 11/1993 | Nakashima et al. |
| 5,407,986 | A | | 4/1995 | Furukawa et al. |
| 5,412,004 | A | | 5/1995 | Tachibana et al. |
| 5,473,041 | A | | 12/1995 | Itoh |
| 5,512,272 | A | | 4/1996 | Krzysik |
| 5,567,428 | A | | 10/1996 | Hughes |
| 5,725,882 | A | | 3/1998 | Kumar et al. |
| 5,837,223 | A | | 11/1998 | Barone et al. |
| 5,851,517 | A | | 12/1998 | Mougin et al. |
| 5,874,069 | A | * | 2/1999 | Mendolia et al. ............... 424/65 |
| 5,919,441 | A | | 7/1999 | Mendolia et al. |
| 5,945,095 | A | | 8/1999 | Mougin et al. |
| 5,969,172 | A | | 10/1999 | Nye |
| 5,981,680 | A | * | 11/1999 | Petroff et al. ................... 528/26 |
| 5,985,297 | A | | 11/1999 | Mellul et al. |
| 6,033,650 | A | | 3/2000 | Calello et al. |
| 6,045,782 | A | | 4/2000 | Krog et al. |
| 6,051,216 | A | | 4/2000 | Barr et al. |
| 6,060,072 | A | | 5/2000 | Konik et al. |
| 6,096,298 | A | * | 8/2000 | Swaile ........................... 424/65 |
| 6,103,250 | A | | 8/2000 | Brieva et al. |
| 6,177,091 | B1 | | 1/2001 | Bara et al. |
| 6,353,076 | B1 | | 3/2002 | Barr et al. |
| 6,362,287 | B1 | | 3/2002 | Chorvath et al. |
| 6,362,288 | B1 | | 3/2002 | Brewer et al. |
| 6,376,078 | B1 | | 4/2002 | Inokuchi |
| 6,423,324 | B1 | | 7/2002 | Murphy et al. |
| 6,426,062 | B1 | | 7/2002 | Chopra et al. |
| 6,451,295 | B1 | | 9/2002 | Cai et al. |
| 6,503,632 | B1 | | 1/2003 | Hayashi et al. |

(Continued)

FOREIGN PATENT DOCUMENTS

| EP | 0 377 447 A2 | 7/1990 |
| EP | 0 594 285 A2 | 4/1994 |

(Continued)

OTHER PUBLICATIONS

English translation of Interrogatory issued in Japanese Application No. 2004-512704.
Office Action issued Jan. 27, 2012, in Japanese Patent Application No. 2008-12092.
Office Action issued Feb. 14, 2012, in European Patent Application No. 03 739 096.0.
Office Action issued Oct. 4, 2012 in European Patent Application No. 03 739 096.0.
Dow Corning 2-8178 Gellant, Product Information, Apr. 16, 2003, 6 pages.
Dow Corning® 2-8178 Gellant, Product Information Personal Care, 6 pp., Aug. 13, 2002.
Dow Corning® 2-8178 Gellant, Ref. No. 27/1055-01, Aug. 2002, 35 pp.
English Language Derwent Abstract of EP 0 923 928, Jun. 23, 1999.
English Language Derwent Abstract of EP 1 068 856, Jan. 17, 2001.
English Language Derwent Abstract of FR 2 765 800, Jan. 15, 1999.

(Continued)

*Primary Examiner* — Janet Epps-Smith
*Assistant Examiner* — Audrea Buckley
(74) *Attorney, Agent, or Firm* — Oblon, Spivak, McClelland, Maier & Neustadt, L.L.P.

(57) ABSTRACT

The invention relates to a physiologically acceptable composition, especially a cosmetic composition, comprising (a) at least one polyorganosiloxane containing polymer comprising at least one moiety which comprises at least one polyorganosiloxane group consisting of 1 to about 1000 organosiloxane units in the chain of the moiety or in the form of graft, and at least two groups capable of establishing hydrogen interactions; (b) at least one volatile alcohol; and (c) at least one thickening agent, as well as to methods of using such compositions and kits containing such compositions.

19 Claims, No Drawings

(56) References Cited

U.S. PATENT DOCUMENTS

| | | | |
|---|---|---|---|
| 6,524,598 B2 | 2/2003 | Sunkel et al. | |
| 6,534,072 B2 | 3/2003 | Mondet et al. | |
| 6,541,017 B1 | 4/2003 | Lemann et al. | |
| 6,569,955 B1 | 5/2003 | Brewer et al. | |
| 6,682,748 B1 | 1/2004 | De La Poterie et al. | |
| 6,743,868 B2 | 6/2004 | Fournier et al. | |
| 6,814,973 B2 | 11/2004 | Mondet | |
| 6,916,464 B2 | 7/2005 | Hansenne et al. | |
| 7,078,026 B2 | 7/2006 | Ferrari et al. | |
| 2001/0031280 A1 | 10/2001 | Ferrari et al. | |
| 2002/0028223 A1 | 3/2002 | Vatter et al. | |
| 2002/0048557 A1* | 4/2002 | Cai et al. | 424/65 |
| 2002/0051758 A1 | 5/2002 | Cai et al. | |
| 2003/0068348 A1 | 4/2003 | Ferrari et al. | |
| 2003/0072730 A1 | 4/2003 | Tournilhac | |
| 2003/0082129 A1* | 5/2003 | Buckingham et al. | 424/70.12 |
| 2003/0170188 A1 | 9/2003 | Ferrari et al. | |
| 2003/0228333 A1 | 12/2003 | Fecht et al. | |
| 2003/0232030 A1 | 12/2003 | Lu et al. | |
| 2003/0235548 A1 | 12/2003 | Lu | |
| 2003/0235552 A1 | 12/2003 | Yu | |
| 2003/0235553 A1 | 12/2003 | Lu et al. | |
| 2004/0001799 A1 | 1/2004 | Lu et al. | |
| 2004/0115153 A1 | 6/2004 | Yu | |
| 2004/0115154 A1 | 6/2004 | Yu | |
| 2004/0120912 A1 | 6/2004 | Yu | |
| 2004/0126336 A1 | 7/2004 | Hansenne et al. | |
| 2004/0170586 A1 | 9/2004 | Ferrari et al. | |
| 2004/0180032 A1 | 9/2004 | Manelski et al. | |
| 2004/0197285 A1 | 10/2004 | Van Dort | |
| 2004/0223936 A1 | 11/2004 | Fecht et al. | |
| 2004/0228890 A1 | 11/2004 | Blin et al. | |
| 2005/0009989 A1 | 1/2005 | Liew et al. | |
| 2005/0020769 A1 | 1/2005 | Lu et al. | |
| 2005/0089492 A1 | 4/2005 | Lu et al. | |
| 2005/0158260 A1 | 7/2005 | Ferrari et al. | |
| 2006/0110345 A1 | 5/2006 | Lu et al. | |
| 2007/0053859 A1 | 3/2007 | Bui et al. | |
| 2008/0171008 A1 | 7/2008 | Bui | |

FOREIGN PATENT DOCUMENTS

| | | | |
|---|---|---|---|
| EP | 0 693 517 A1 | 1/1996 | |
| EP | 0 709 083 | 5/1996 | |
| EP | 0 923 928 | 6/1999 | |
| EP | 1 048 686 | 11/2000 | |
| EP | 1 068 856 | 1/2001 | |
| EP | 1 114 636 | 7/2001 | |
| EP | 1 266 647 | 12/2002 | |
| EP | 1 266 648 | 12/2002 | |
| EP | 1 266 653 | 12/2002 | |
| EP | 1 854 450 | 11/2007 | |
| FR | 2 765 800 | 1/1999 | |
| FR | 2 825 914 | 12/2002 | |
| FR | 2 825 915 | 12/2002 | |
| FR | 2 825 916 | 12/2002 | |
| GB | 134 8783 | 3/1974 | |
| JP | 55-105609 | 8/1980 | |
| JP | 02-25411 | 1/1990 | |
| JP | 06-279253 | 10/1994 | |
| JP | 08-239316 | 10/1994 | |
| JP | 09-071505 | 3/1997 | |
| JP | 11-236314 | 8/1999 | |
| JP | 2000-038450 | 2/2000 | |
| JP | 2001-081009 | 3/2001 | |
| JP | 2001-81009 | 3/2001 | |
| JP | 2001-503070 | 3/2001 | |
| JP | 2001-206821 | 7/2001 | |
| JP | 2001-512164 | 8/2001 | |
| JP | 2001-316244 | 11/2001 | |
| JP | 2002-12514 | 1/2002 | |
| JP | 2002-173459 | 6/2002 | |
| JP | 2002-173460 | 6/2002 | |
| JP | 2002-173464 | 6/2002 | |
| JP | 2006-502101 | 1/2006 | |
| WO | WO 97/36572 | 10/1997 | |
| WO | WO 97/36573 | 10/1997 | |
| WO | WO97/36573 | * 10/1997 | 424/401 |
| WO | WO 99/47111 | 1/1999 | |
| WO | WO 99/06473 | 2/1999 | |
| WO | WO99/22710 | 5/1999 | |
| WO | WO 00/09587 | 2/2000 | |
| WO | WO 01/09239 A1 | 2/2001 | |
| WO | WO 01/97758 A2 | 12/2001 | |
| WO | WO 02/17870 A2 | 3/2002 | |
| WO | WO 02/17871 A2 | 3/2002 | |
| WO | WO 02/089760 A1 | 11/2002 | |
| WO | WO 03/013447 A2 | 2/2003 | |
| WO | WO 03/105788 A2 | 6/2003 | |
| WO | WO 03/101412 | 12/2003 | |
| WO | WO 03/105789 | 12/2003 | |
| WO | WO 03/105798 A1 | 12/2003 | |
| WO | WO 2004/054523 | 7/2004 | |
| WO | WO 2004/054524 | 7/2004 | |
| WO | WO 2005/060922 | 7/2005 | |

OTHER PUBLICATIONS

European Patent Office Communication dated Aug. 18, 2008 from European Application No. 07 150 485.6-2108, 4 pages.

Notice of Reasons for Rejection from Japanese Application No. 2005-502446, Mailed Jan. 30, 2007, 4 pp.

Notice of Reasons for Rejection from Japanese Application No. 2005-502445, Drafted Jan. 25, 2007, Mailed Jan. 30, 2007, 3 pp.

Notice of Rejection for Japanese Patent Application 2004-512707 issued Jun. 6, 2006 (w/English Translation).

Office Action dated Oct. 21, 2010, in European Application No. 03739096.0.

Office Action issued Oct. 5, 2010, in Japanese Application No. 2004-512707 (English Translation).

Shin-Etsu Silicones for Personal Care; Product Brochure, KSP-100•101•102•103•104•105 "Hybrid Silicone Powders for Personal Care" 2000.

Shin-Etsu Silicones for Personal Care; Product Brochure, KSP-200•300 "Hybrid Silicone Powders containing Fluoroalkyl or Phenyl group for Personal Care" 2001.

Silicone Polyamide: An Innovative Structurant for Personal Care Applications; XP-002476529; Dow Corning, 2003.

Office Action issued Jun. 6, 2012, in Mexican Patent Application No. MX/a/2007/016506.

Office Action issued Apr. 20, 2011, in Chinese Application No. 03813776.3.

* cited by examiner

COMPOSITION CONTAINING A POLYORGANOSILOXANE POLYMER, A THICKENING AGENT AND AT LEAST ONE VOLATILE ALCOHOL

CROSS-REFERENCE TO RELATED APPLICATIONS

This application is a continuation-in-part of U.S. Ser. No. 11/967,414, filed Dec. 31, 2007, and claims the benefit of U.S. Ser. No. 60/882,697, filed Dec. 29, 2006. This application is also a continuation-in-part of Ser. No. 10/538,924, filed Jun. 13, 2005, which is the National Stage of PCT/EP03/15006, filed Dec. 8, 2003, and claims the benefit of U.S. Ser. No. 60/438,782, filed Jan. 9, 2003, the entire contents of these applications are hereby incorporated by reference.

FIELD OF THE INVENTION

The present invention relates to compositions, for example, a transfer resistant cosmetic composition, which may also be pliable and/or comfortable to wear upon application to a keratinous substrate, comprising at least one polyorganosiloxane containing polymer comprising at least one moiety comprising at least one polyorganosiloxane group comprising organosiloxane units in the chain of the moiety or in the form of a graft, and at least two groups capable of establishing hydrogen interactions, at least one volatile alcohol and at least one thickening agent.

DISCUSSION OF THE BACKGROUND

Many cosmetic compositions, including pigmented cosmetics such as foundations, concealers, lipsticks, and mascaras, and other cosmetic and sunscreen compositions, have been developed for longer wear and transfer resistance properties. This is generally accomplished by the use of compositions that form a film after application. Such compositions generally contain volatile solvents, which evaporate on contact with the skin or other keratinous tissue, leaving behind a layer comprising waxes and/or resins, pigments, fillers, and actives. However, these compositions tend to be uncomfortable for the wearer as the composition remains on the skin or other keratinous tissue as a brittle or non-flexible film. Such compositions may not be pliable or soft, and they may not be comfortable to wear. There may also be a tendency for such compositions to flake off because of poor adherence to the skin or other keratinous tissue. Furthermore, such compositions have a tendency to be tacky, resulting in poor application, spreadability and wear characteristics.

U.S. Pat. No. 5,874,069, U.S. Pat. No. 5,919,441, U.S. Pat. No. 6,051,216, U.S. Pat. No. 6,353,076, WO-A-02/17870 and WO-A-02/17871, disclose non-liquid (semi-solid, soft-solid, solid) deodorant gels or sticks containing polyorganosiloxane containing polymers. Such deodorant sticks and gels, however, are unacceptable for cosmetic applications, particularly for cosmetic applications in which color transfer-resistance is desired.

Thus, there remains a need for improved long-wearing cosmetic compositions which transfer little or not at all, i.e., "transfer-free" or transfer resistant compositions which also possess good cosmetic properties such as pliability and comfort. For example, a composition that is transfer resistant may deposit a film onto a keratinous substance that may not transfer when the keratinous substance comes into contact with, for example, skin, clothes, a cup, paper, cigarette, or a handkerchief.

Accordingly, one aspect of the present invention is a care and/or makeup and/or treatment composition for keratinous material such as skin, hair, eyelashes, nails and/or lips, which is able to address or overcome at least one of the aforementioned problems with the prior art compositions.

SUMMARY OF THE INVENTION

The present invention relates to compositions, preferably cosmetic compositions, comprising at least one polyorganosiloxane containing polymer chosen from homopolymers and copolymers, at least one volatile alcohol and at least one thickening agent. Preferably the compositions further comprise at least one volatile oil.

The present invention also relates to colored cosmetic compositions comprising at least one polyorganosiloxane containing polymer, preferably a silicone-polyamide copolymer, at least one coloring agent, at least one volatile alcohol and at least one thickening agent. Preferably the compositions further comprise at least one volatile oil. Such colored cosmetic compositions can be anhydrous lip compositions (for example, lipstick or liquid lip colors) or foundations.

The present invention further relates to colored cosmetic compositions comprising at least one polyorganosiloxane containing polymer, preferably a silicone-polyamide copolymer, at least one coloring agent, at least one volatile alcohol, at least one thickening agent and water. Preferably the compositions further comprise at least one volatile oil. Such water-containing colored cosmetic compositions are preferably lip compositions (for example, lipstick or liquid lip colors), foundations or mascaras, and are emulsions or dispersions.

The present invention also relates to methods of treating, caring for and/or making up keratinous material (for example, skin or lips) by applying compositions of the present invention to the keratinous material in an amount sufficient to treat, care for and/or make up the keratinous material.

The present invention further relates to covering or hiding skin defects associated with keratinous material (for example, skin or lips) by applying compositions of the present invention to the keratinous material in an amount sufficient to cover or hide such skin defects.

The present invention also relates to methods of enhancing the appearance of keratinous material (for example, skin or lips) by applying compositions of the present invention to the keratinous material in an amount sufficient to enhance the appearance of the keratinous material.

The present invention further relates to compositions having improved cosmetic properties such as, for example, improved long wear, transfer resistance and/or waterproof properties. The compositions may also possess improved feel upon application (for example, more comfortable deposit), flexibility, wearability, drying time and/or retention as well as reduced tackiness and/or migration over time.

The present invention also relates to kits comprising (a) a composition comprising at least one polyorganosiloxane containing polymer, preferably a silicone-polyimide copolymer, at least one coloring agent, at least one volatile alcohol and at least one thickening agent; and (b) a basecoat and/or topcoat composition. Preferably composition (a) further comprises at least one volatile oil.

The present invention also relates to methods of making a non-liquid composition, preferably a solid composition, comprising mixing at least one polyorganosiloxane containing polymer, preferably a silicone-polyamide copolymer, with at least one volatile alcohol and at least one thickening agent to form a non-liquid composition.

It is to be understood that both the foregoing general description and the following detailed description are exemplary and explanatory only, and are not restrictive of the invention.

DETAILED DESCRIPTION OF THE INVENTION

As used herein, the expression "at least one" means one or more and thus includes individual components as well as mixtures/combinations.

"Film former" or "film forming agent" as used herein means a polymer or resin that leaves a film on the substrate to which it is applied, for example, after a solvent accompanying the film former has evaporated, absorbed into and/or dissipated on the substrate.

"Transfer resistance" as used herein refers to the quality exhibited by compositions that are not readily removed by contact with another material, such as, for example, a glass, an item of clothing or the skin, for example, when eating or drinking. Transfer resistance may be evaluated by any method known in the art for evaluating such. For example, transfer resistance of a composition may be evaluated by a "kiss" test. The "kiss" test may involve application of the composition to human keratin material such as hair, skin or lips followed by rubbing a material, for example, a sheet of paper, against the hair, skin or lips after expiration of a certain amount of time following application, such as 2 minutes after application. Similarly, transfer resistance of a composition may be evaluated by the amount of product transferred from a wearer to any other substrate, such as transfer from the hair, skin or lips of an individual to a collar when putting on clothing after the expiration of a certain amount of time following application of the composition to the hair, skin or lips. The amount of composition transferred to the substrate (e.g., collar, or paper) may then be evaluated and compared. For example, a composition may be transfer resistant if a majority of the product is left on the wearer's hair, skin or lips. Further, the amount transferred may be compared with that transferred by other compositions, such as commercially available compositions. In a preferred embodiment of the present invention, little or no composition is transferred to the substrate from the hair, skin or lips.

"Long wear" compositions as used herein, refers to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to human hair, skin or lips and evaluating the color of the composition after an extended period of time. For example, the color of a composition may be evaluated immediately following application to hair, skin or lips and these characteristics may then be re-evaluated and compared after a certain amount of time. Further, these characteristics may be evaluated with respect to other compositions, such as commercially available compositions.

"Tackiness" as used herein refers to the adhesion between two substances. For example, the more tackiness there is between two substances, the more adhesion there is between the substances. To quantify "tackiness," it is useful to determine the "work of adhesion" as defined by IUPAC associated with the two substances. Generally speaking, the work of adhesion measures the amount of work necessary to separate two substances. Thus, the greater the work of adhesion associated with two substances, the greater the adhesion there is between the substances, meaning the greater the tackiness is between the two substances.

Work of adhesion and, thus, tackiness, can be quantified using acceptable techniques and methods generally used to measure adhesion, and is typically reported in units of force time (for example, gram seconds ("g s")). For example, the TA-XT2 from Stable Micro Systems, Ltd. can be used to determine adhesion following the procedures set forth in the TA-XT2 Application Study (ref: MATI/PO.25), revised January 2000, the entire contents of which are hereby incorporated by reference. According to this method, desirable values for work of adhesion for substantially non-tacky substances include less than about 0.5 g s, less than about 0.4 g s, less than about 0.3 g s and less than about 0.2 g s. As known in the art, other similar methods can be used on other similar analytical devices to determine adhesion.

"Waterproof" as used herein refers to the ability to repel water and permanence with respect to water. Waterproof properties may be evaluated by any method known in the art for evaluating such properties. For example, a mascara composition may be applied to false eyelashes, which may then be placed in water for a certain amount of time, such as, for example, 20 minutes. Upon expiration of the pre-ascertained amount of time, the false eyelashes may be removed from the water and passed over a material, such as, for example, a sheet of paper. The extent of residue left on the material may then be evaluated and compared with other compositions, such as, for example, commercially available compositions. Similarly, for example, a composition may be applied to skin, and the skin may be submerged in water for a certain amount of time. The amount of composition remaining on the skin after the pre-ascertained amount of time may then be evaluated and compared. For example, a composition may be waterproof if a majority of the product is left on the wearer, e.g., eyelashes, skin, etc. In a preferred embodiment of the present invention, little or no composition is transferred from the wearer.

The cosmetic compositions and methods of the present invention can comprise, consist of, or consist essentially of the essential elements and limitations of the invention described herein, as well as any additional or optional ingredients, components, or limitations described herein or otherwise useful in personal care compositions intended for topical application to hair.

The composition of the present invention may be in any form, either liquid or non-liquid (semi-solid, soft solid, solid, etc.). For example, it may be a paste, a solid, a gel, or a cream. It may be an emulsion, such as an oil-in-water or water-in-oil emulsion, a multiple emulsion, such as an oil-in-water-in-oil emulsion or a water-in-oil-in-water emulsion, or a solid, rigid or supple gel, including anhydrous gels. The composition can also be in a form chosen from a translucent anhydrous gel and a transparent anhydrous gel. The composition of the invention may, for example, comprise an external or continuous fatty phase. The composition may be anhydrous. The composition can also be a molded composition or cast as a stick or a dish. The composition in one embodiment is a solid such as a molded stick or a poured stick.

Depending on the intended application, such as a stick, hardness of the composition may also be considered. The hardness of a composition may, for example, be expressed in gramforce (gf). The composition of the present invention may, for example, have a hardness ranging from 20 gf to 2000 gf, such as from 20 gf to 900 gf, and further such as from 20 gf to 600 gf.

This hardness is measured in one of two ways. A first test for hardness is according to a method of penetrating a probe into the composition and in particular using a texture analyzer (for example TA-XT2i from Rheo) equipped with an ebonite cylinder of height 25 mm and diameter 8 mm. The hardness measurement is carried out at 20° C. at the center of 5 samples of the composition. The cylinder is introduced into each sample of composition at a pre-speed of 2 mm/s and then at a speed of 0.5 mm/s and finally at a post-speed of 2 mm/s, the total displacement being 1 mm. The recorded hardness value is that of the maximum peak observed. The measurement error is ±50 gf.

The second test for hardness is the "cheese wire" method, which involves cutting an 8.1 mm or preferably 12.7 mm in diameter stick composition and measuring its hardness at 20° C. using a DFGHS 2 tensile testing machine from Indelco-Chatillon Co. at a speed of 100 mm/minute. The hardness value from this method is expressed in grams as the shear force required to cut a stick under the above conditions. According to this method, the hardness of compositions according to the present invention which may be in stick form may, for example, range from 30 g to 300 g, such as from 30 g to 250 g, for a sample of 8.1 mm in diameter stick, and further such as from 30 g to 200 g, and also further such as from 30 g to 120 g for a sample of 12.7 mm in diameter stick.

The hardness of the composition of the present invention may be such that the compositions are self-supporting and can easily disintegrate to form a satisfactory deposit on keratin materials. In addition, this hardness may impart good impact strength to the inventive compositions, which may be molded or cast, for example, in stick or dish form.

The skilled artisan may choose to evaluate a composition using at least one of the tests for hardness outlined above based on the application envisaged and the hardness desired. If one obtains an acceptable hardness value, in view of the intended application, from at least one of these hardness tests, the composition falls within preferred embodiments of the invention.

As is evident, the hardness of the composition according to preferred embodiments of the invention may, for example, be such that the composition is advantageously self-supporting and can disintegrate easily to form a satisfactory deposit on keratin materials. In addition, with this hardness, the composition of the invention may have good impact strength.

According to preferred embodiments of the present invention, the composition in stick form may have the behavior of a deformable, flexible elastic solid, giving noteworthy elastic softness on application.

As defined herein, stability is tested by placing the composition in a controlled environment chamber for 8 weeks at 25° C. In this test, the physical condition of the sample is inspected as it is placed in the chamber. The sample is then inspected again at 24 hours, 3 days, 1 week, 2 weeks, 4 weeks and 8 weeks. At each inspection, the sample is examined for abnormalities in the composition such as phase separation if the composition is in the form of an emulsion, bending or leaning if the composition is in stick form, melting, or syneresis (or sweating). The stability is further tested by repeating the 8-week test at 25° C., 37° C., 45° C. and under freeze-thaw conditions. A composition is considered to lack stability if in any of these tests an abnormality that impedes functioning of the composition is observed. The skilled artisan will readily recognize an abnormality that impedes functioning of a composition based on the intended application.

Polyorganosiloxane Containing Polymer

According to the present invention, compositions comprising at least one polyorganosiloxane containing polymer chosen from homopolymers and copolymers, preferably, with a weight-average molecular mass ranging from about 500 g/mol to about 2.5×10$^6$ g/mol or more, comprising at least one moiety comprising: at least one polyorganosiloxane group comprising, preferably, from 1 to about 10,000 organosiloxane units in the chain of the moiety or in the form of a graft, and at least two groups capable of establishing hydrogen interactions are provided. Preferably, the polyorganosiloxane-containing copolymer is a silicone-polyamide copolymer: that is, a copolymer containing both silicone and amide moieties.

According to preferred embodiments of the present invention, the polyorganosiloxane-containing polymers used in the composition of the invention may belong to the following two families:

a) polyorganosiloxanes comprising at least two groups capable of establishing hydrogen interactions, these two groups being located in the polymer chain; and/or b) polyorganosiloxanes comprising at least two groups capable of establishing hydrogen interactions, these two groups being located on grafts or branches.

The polyorganosiloxane containing polymers of the present invention can be liquid or solid at room temperature. Preferably, the polymers are solid. When the polymers are solid, it is preferable that they can be dissolved before or during use in a solvent with hydrogen interaction capable of breaking the hydrogen interactions of the polymers, for instance $C_2$ to $C_8$ lower alcohols and especially ethanol, n-propanol or isopropanol. It is also possible to use these hydrogen interaction "breaking" solvents as co-solvents in the compositions of the present invention. These solvents may then be stored in the composition or may be removed by selective evaporation, which is well known to those skilled in the art.

The polymers comprising two groups capable of establishing hydrogen interactions in the polymer chain may be polymers comprising at least one moiety corresponding to the formula:

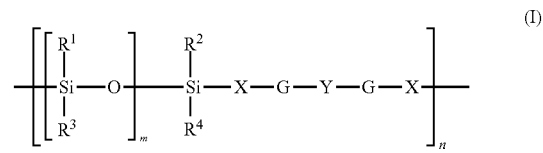

(I)

in which:

1) $R^1$, $R^2$, $R^3$ and $R^4$, which may be identical or different, represent a group chosen from:

linear, branched or cyclic, saturated or unsaturated, $C_1$ to $C_{40}$ hydrocarbon-based groups, possibly containing in their chain one or more oxygen, sulphur and/or nitrogen atoms, and possibly being partially or totally substituted with fluorine atoms, $C_6$ to $C_{10}$ aryl groups, optionally substituted with one or more $C_1$ to $C_4$ alkyl groups, polyorganosiloxane chains possibly containing one or more oxygen, sulphur and/or nitrogen atoms;

2) the groups X, which may be identical or different, represent a linear or branched $C_1$ to $C_{30}$ alkylenediyl group, possibly containing in its chain one or more oxygen and/or nitrogen atoms;

3) Y is a saturated or unsaturated, $C_1$ to $C_{50}$ linear or branched divalent alkylene, arylene, cycloalkylene, alkylarylene or arylalkylene group, possibly comprising one or more oxygen, sulphur and/or nitrogen atoms, and/or bearing as substituent one of the following atoms or groups of atoms:

fluorine, hydroxyl, $C_3$ to $C_8$ cycloalkyl, $C_1$ to $C_{40}$ alkyl, $C_5$ to $C_{10}$ aryl, phenyl optionally substituted with 1 to 3 $C_1$ to $C_3$ alkyl groups, $C_1$ to $C_3$ hydroxyalkyl and $C_1$ to $C_6$ aminoalkyl, or 4) Y represents a group corresponding to the formula:

in which

T represents a linear or branched, saturated or unsaturated, $C_3$ to $C_{24}$ trivalent or tetravalent hydrocarbon-based group optionally substituted with a polyorganosiloxane chain, and possibly containing one or more atoms chosen from O, N and S, or T represents a trivalent atom chosen from N, P and Al, and $R^5$ represents a linear or branched $C_1$ to $C_{50}$ alkyl group or a polyorganosiloxane chain, possibly comprising one or more ester, amide, urethane, thiocarbamate, urea, thiourea and/or sulphonamide groups, which may be linked to another chain of the polymer;

5) the groups G, which may be identical or different, represent divalent groups chosen from:

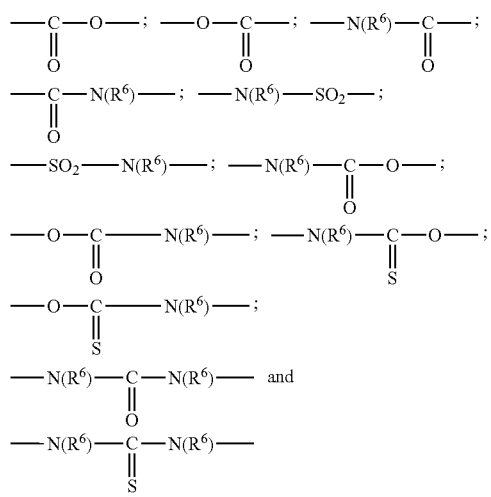

in which $R^6$ represents a hydrogen atom or a linear or branched $C_1$ to $C_{20}$ alkyl group, on condition that at least 50% of the groups $R^6$ of the polymer represents a hydrogen atom and that at least two of the groups G of the polymer are a group other than:

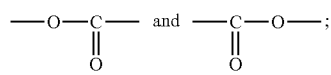

6) n is an integer of at least 1, for example ranging from 2 to 500 and preferably from 2 to 200, and m is an integer of at least one, ranging from 1 to 35,000, for example, from 1 to 10,000 and 1 to 2,500, from 1 to 700 and from 6 to 200, including all values and subranges there between.

According to the invention, 80% of the groups $R^1$, $R^2$, $R^3$ and $R^4$ of the polymer are preferably chosen from methyl, ethyl, phenyl and 3,3,3-trifluoropropyl groups.

According to the invention, Y can represent various divalent groups, furthermore optionally comprising one or two free valencies to establish bonds with other moieties of the polymer or copolymer. Preferably, Y represents a group chosen from:

a) linear $C_1$ to $C_{20}$ and preferably $C_1$ to $C_{10}$ alkylene groups, b) $C_{30}$ to $C_{56}$ branched alkylene groups possibly comprising rings and unconjugated unsaturations, c) $C_5$-$C_6$ cycloalkylene groups, d) phenylene groups optionally substituted with one or more $C_1$ to $C_{40}$ alkyl groups, e) $C_1$ to $C_{20}$ alkylene groups comprising from 1 to 5 amide groups, f) $C_1$ to $C_{20}$ alkylene groups comprising one or more substituents chosen from hydroxyl, $C_3$ to $C_8$ cycloalkane, $C_1$ to $C_3$ hydroxyalkyl and $C_1$ to $C_6$ alkylamine groups, g) polyorganosiloxane chains of formula:

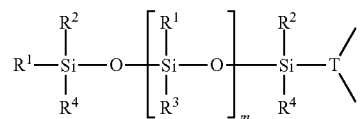

in which $R^1$, $R^2$, $R^3$, $R^4$, T and m are as defined above, and h) polyorganosiloxane chains of formula:

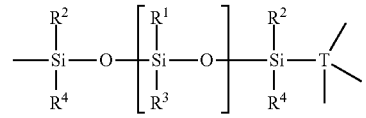

The polyorganosiloxanes of the second family may be polymers comprising at least one moiety corresponding to formula (II):

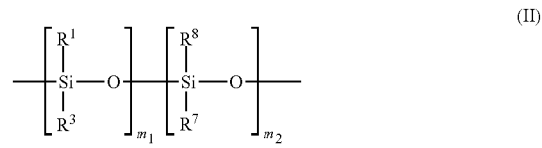

(II)

in which $R^1$ and $R^3$, which may be identical or different, are as defined above for formula (I), $R^7$ represents a group as defined above for $R^1$ and $R^3$, or represents a group of formula —X-G-$R^9$ in which X and G are as defined above for formula (I) and $R^9$ represents a hydrogen atom or a linear, branched or cyclic, saturated or unsaturated, $C_1$ to $C_{50}$ hydrocarbon-based group optionally comprising in its chain one or more atoms chosen from O, S and N, optionally substituted with one or more fluorine atoms and/or one or more hydroxyl groups, or a phenyl group optionally substituted with one or more $C_1$ to $C_4$ alkyl groups, $R^8$ represents a group of formula —X-G-$R^9$ in which X, G and $R^9$ are as defined above, $m_1$ is an integer of at least one ranging from 1 to 35,000, for example, from 1 to 10,000 and 1 to 2,500, from 1 to 700, and from 6 to 200, including all values and subranges there between; and $m_2$ is an integer of at least one ranging from 1 to 35,000, for example, from 1 to 10,000 and 1 to 2,500, from 1 to 700, and from 6 to 200, including all values and subranges there between.

According to the invention, the polyorganosiloxane containing polymer may be a homopolymer, that is to say a polymer comprising several identical moieties, in particular moieties of formula (I) or of formula (II).

According to the invention, it is also possible to use a polymer consisting of a copolymer comprising several different moieties of formula (I), that is to say a polymer in which at least one of the groups $R^1$, $R^2$, $R^3$, $R^4$, X, G, Y, m and n is different in one of the moieties. The copolymer may also be formed from several moieties of formula (II), in which at least one of the groups $R^1$, $R^3$, $R^7$, $R^8$, $m_1$ and $m_2$ is different in at least one of the moieties.

It is also possible to use a copolymer comprising at least one moiety of formula (I) and at least one moiety of formula (II), the moieties of formula (I) and the moieties of formula (II) possibly being identical to or different from each other.

According to preferred embodiments, it is also possible to use a copolymer comprising at least one hydrocarbon-based moiety comprising two groups capable of establishing hydrogen interactions, chosen from ester, amide, sulphonamide, carbamate, thiocarbamate, urea and thiourea groups, and combinations thereof.

These copolymers may be block copolymers or grafted copolymers.

According to a first embodiment of the invention, the groups capable of establishing hydrogen interactions are amide groups of formulae —C(O)NH— and —HN—C(O)—.

In this case, the polymer may comprise at least one moiety of formula (III) or (IV):

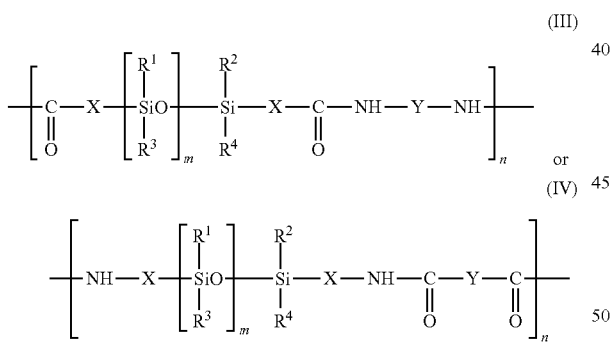

in which $R^1$, $R^2$, $R^3$, $R^4$, X, Y, m and n are as defined above.

Such a moiety may be obtained:

either by a condensation reaction between a silicone containing α,ω-carboxylic acid ends and one or more diamines, according to the following reaction scheme:

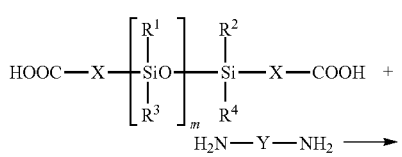

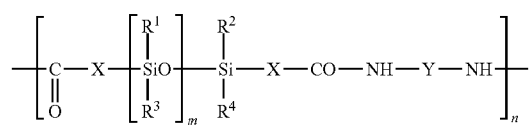

or by reaction of two molecules of a-unsaturated carboxylic acid with a diamine according to the following reaction scheme:

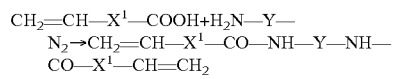

followed by the addition of a siloxane to the ethylenic unsaturations, according to the following scheme:

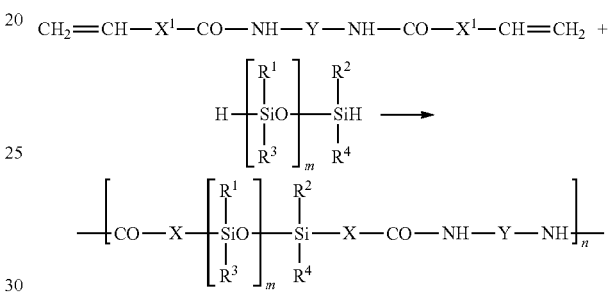

in which $X^1$—$(CH_2)_2$— corresponds to X defined above and Y, $R^1$, $R^2$, $R^3$, $R^4$ and m are as defined above;

or by reaction of a silicone containing α,ω-$NH_2$ ends and a diacid of formula HOOC—Y—COOH according to the following reaction scheme:

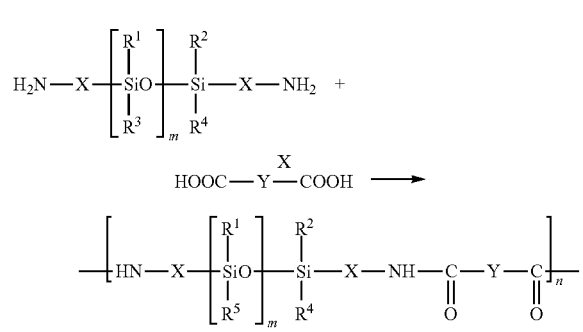

In these polyamides of formula (III) or (IV), m is an integer of at least one as defined above, and preferably in the range from 1 to 700, for example, from 15 to 500 and from 15 to 45, including all values and subranges there between; and n is in particular in the range from 1 to 500, for example, from 1 to 100 and from 4 to 25, including all values and subranges there between; X is preferably a linear or branched alkylene chain containing from 1 to 30 carbon atoms and in particular 3 to 10 carbon atoms, and Y is preferably an alkylene chain that is linear or branched or that possibly comprises rings and/or unsaturations, containing from 1 to 40 carbon atoms, including from 1 to 20 carbon atoms and from 2 to 6 carbon atoms, including all values and subranges there between, for example, 6 carbon atoms.

In formulae (III) and (IV), the alkylene group representing X or Y can optionally contain in its alkylene portion at least one of the following elements:

1) 1 to 5 amide, urea or carbamate groups,
2) a $C_5$ or $C_6$ cycloalkyl group, and
3) a phenylene group optionally substituted with 1 to 3 identical or different $C_1$ to $C_3$ alkyl groups.

In formulae (III) and (IV), the alkylene groups may also be substituted with at least one element chosen from the group consisting of:

a hydroxyl group,
a $C_3$ to $C_8$ cycloalkyl group,
one to three $C_1$ to $C_{40}$ alkyl groups,
a phenyl group optionally substituted with one to three $C_1$ to $C_3$ alkyl groups,
a $C_1$ to $C_3$ hydroxyalkyl group, and
a $C_1$ to $C_6$ aminoalkyl group.

In these formulae (III) and (IV), Y may also represent:

in which $R^5$ represents a polyorganosiloxane chain and T represents a group of formula:

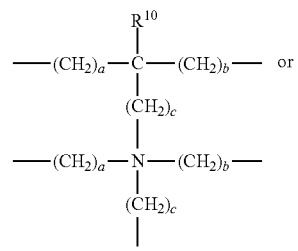

in which a, b and c are, independently, integers ranging from 1 to 10, and $R^{10}$ is a hydrogen atom or a group such as those defined for $R^1$, $R^2$, $R^3$ and $R^4$.

In formulae (III) and (IV), $R^1$, $R^2$, $R^3$ and $R^4$ preferably represent, independently, a linear or branched $C_1$ to $C_{40}$ alkyl group, preferably a $CH_3$, $C_2H_5$, n-$C_3H_7$ or isopropyl group, a polyorganosiloxane chain or a phenyl group optionally substituted with one to three methyl or ethyl groups.

As has been seen previously, the polymer may comprise identical or different moieties of formula (III) or (IV).

Thus, the polymer may be a polyamide containing several moieties of formula (III) or (IV) of different lengths, i.e. a polyamide corresponding to the formula:

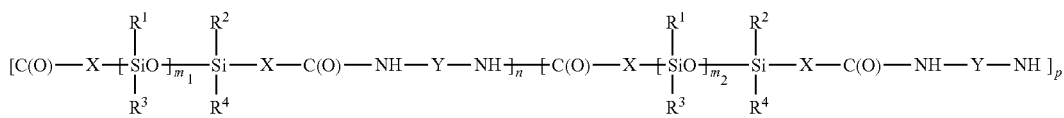

(V)

in which X, Y, n and $R^1$ to $R^4$ have the meanings given above, $m_1$ and $m_2$, which are different, are as defined above, and preferably are chosen in the range from 1 to 1 000, and p is at least one for example ranging from 2 to 500 and preferably from 2 to 200.

In this formula, the moieties may be structured to form either a block copolymer, or a random copolymer or an alternating copolymer. In this copolymer, the moieties may be not only of different lengths, but also of different chemical structures, for example containing different groups Y. In this case, the copolymer may correspond to the formula:

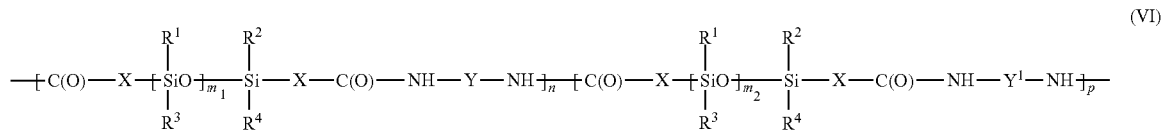

(VI)

in which $R^1$ to $R^4$, X, Y, $m_1$, $m_2$, n and p have the meanings given above and $Y^1$ is different from Y but chosen from the groups defined for Y. As previously discussed, the various moieties may be structured to form either a block copolymer, or a random copolymer or an alternating copolymer.

In an embodiment of the invention, the polyorganosiloxane-containing polymer may also contain a grafted copolymer. Thus, the polyimide containing silicone units may be grafted and optionally crosslinked with silicone chains containing amide groups. Such polymers may be synthesized with trifunctional amines.

In this case, the copolymer may comprise at least one moiety of formula:

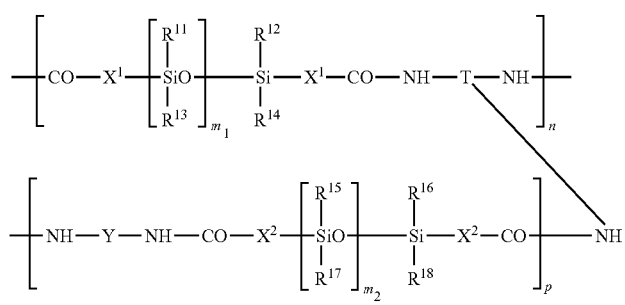

(VII)

in which $X^1$ and $X^2$, which may be identical or different, have the meaning given for X in formula (I), n is as defined in formula (I), Y and T are as defined in formula (I), $R^{11}$ to $R^{18}$ are groups chosen from the same group as $R^1$ to $R^4$, $m_1$ and $m_2$ are numbers in the range from 1 to 1,000, and p is an integer of at least one, for example, p can range from 2 to 500.

In formula (VII), it is preferred that:

p is in the range from 1 to 25, including from 1 to 7, including all values and subranges there between, $R^{11}$ to $R^{18}$ are methyl groups, T corresponds to one of the following formulae:

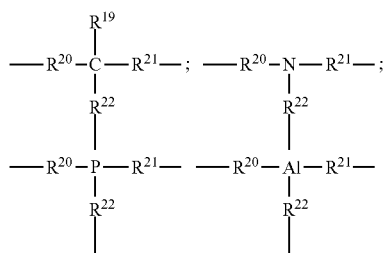

in which $R^{19}$ is a hydrogen atom or a group chosen from the groups defined for $R^1$ to $R^4$, and $R^{20}$, $R^{21}$ and $R^{22}$ are, independently, linear or branched alkylene groups, and more preferably corresponds to the formula:

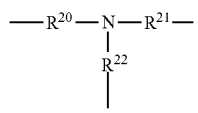

in particular with $R^{20}$, $R^{21}$ and $R^{22}$ representing —$CH_2$—$CH_2$—, $m_1$ and $m_2$ are in the range from 15 to 500, including from 15 to 45 and including all values and subranges there between, $X^1$ and $X^2$ represent —$(CH_2)_{10}$—, and Y represents —$CH_2$—.

These polyamides containing a grafted silicone moiety of formula (VII) may be copolymerized with polyamide-silicones of formula (II) to form block copolymers, alternating copolymers or random copolymers. The weight percentage of grafted silicone moieties (VII) in the copolymer may range from 0.5% to 30% by weight.

According to the invention, as has been seen previously, the siloxane units may be in the main chain or backbone of the polymer, but they may also be present in grafted or pendent chains. In the main chain, the siloxane units may be in the form of segments as described above. In the pendent or grafted chains, the siloxane units may appear individually or in segments.

According to the invention, the preferred siloxane-based polyamides are:

polyamides of formula (III) in which m is from 15 to 300, for example, 15 to 100, including all values and subranges there between;

mixtures of two or more polyamides in which at least one polyamide has a value of m in the range from 15 to 50, including all values and subranges there between and at least one polyamide has a value of m in the range from 30 to 300, including all values and subranges there between;

polymers of formula (V) with $m_1$ chosen in the range from 15 to 50 and $m_2$ chosen in the range from 30 to 500 with the portion corresponding to $m_1$ representing 1% to 99% by weight of the total weight of the polyamide and the corresponding portion $m_2$ representing 1% to 99% by weight of the total weight of the polyamide;

mixtures of polyamide of formula (III) combining
1) 80% to 99% by weight of a polyamide in which n is equal to 2 to 10 and in particular 3 to 6, and
2) 1% to 20% of a polyamide in which n is in the range from 5 to 500 and in particular from 6 to 100;

polyamides corresponding to formula (VI) in which at least one of the groups Y and $Y^1$ contains at least one hydroxyl substituent;

polyamides of formula (III) synthesized with at least one portion of an activated diacid (diacid chloride, dianhydride or diester) instead of the diacid;

polyamides of formula (III) in which X represents —$(CH_2)_3$— or —$(CH_2)_{10}$; and polyamides of formula (III) in which the polyamides end with a monofunctional chain chosen from the group consisting of monofunctional amines, monofunctional acids, monofunctional alcohols, including fatty acids, fatty alcohols and fatty amines, such as, for example, octylamine, octanol, stearic acid and stearyl alcohol.

According to the invention, the end groups of the polymer chain may end with:

a $C_1$ to $C_{50}$ alkyl ester group by introducing a $C_1$ to $C_{50}$ monoalcohol during the synthesis, a $C_1$ to $C_{50}$ alkylamide group by taking as stopping group a monoacid if the silicone is α,ω-diaminated, or a monoamine if the silicone is an α,ω-dicarboxylic acid.

According to one embodiment of the invention, it is possible to use a copolymer of silicone polyamide and of hydrocarbon-based polyamide, i.e. a copolymer comprising moieties of formula (III) or (IV) and hydrocarbon-based polyamide moieties. In this case, the polyamide-silicone moieties may be arranged at the ends of the hydrocarbon-based polyamide.

Polyamide-based polymers containing silicones may be produced by silylic amidation of polyamides based on fatty acid dimer. This approach involves the reaction of free acid sites existing on a polyamide as end sites, with organosiloxane-monoamines and/or organosiloxane-diamines (amidation reaction), or alternatively with oligosiloxane alcohols or oligosiloxane diols (esterification reaction). The esterification reaction requires the presence of acid catalysts, as is known in the art. It is desirable for the polyamide containing free acid sites, used for the amidation or esterification reaction, to have a relatively high number of acid end groups (for example polyamides with high acid numbers, for example from 15 to 20).

For the amidation of the free acid sites of the hydrocarbon-based polyamides, siloxane diamines with 1 to 300, more particularly 2 to 50 and for example, 2, 6, 9.5, 12, 13.5, 23 or 31 siloxane groups, may be used for the reaction with hydrocarbon-based polyamides based on fatty acid dimers. Siloxane diamines containing 13.5 siloxane groups are preferred, and the best results are obtained with the siloxane diamine containing 13.5 siloxane groups and polyamides containing high numbers of carboxylic acid end groups.

The reactions may be carried out in xylene to extract the water produced from the solution by azeotropic distillation, or at higher temperatures (about 180 to 200° C.) without solvent. Typically, the efficacy of the amidation and the reaction rates decrease when the siloxane diamine is longer, that is to say when the number of siloxane groups is higher. Free amine sites may be blocked after the initial amidation reaction of the diaminosiloxanes by reacting them either with a siloxane acid, or with an organic acid such as benzoic acid.

For the esterification of the free acid sites on the polyamides, this may be performed in boiling xylene with about 1% by weight, relative to the total weight of the reagents, of para-toluenesulphonic acid as catalyst.

These reactions carried out on the carboxylic acid end groups of the polyamide lead to the incorporation of silicone moieties only at the ends of the polymer chain.

It is also possible to prepare a copolymer of polyamide-silicone, using a polyamide containing free amine groups, by amidation reaction with a siloxane containing an acid group.

It is also possible to prepare a gelling agent based on a copolymer between a hydrocarbon-based polyamide and a silicone polyamide, by transamidation of a polyamide having, for example, an ethylene-diamine constituent, with an oligosiloxane-α,ω-diamine, at high temperature (for example 200 to 300° C.), to carry out a transamidation such that the ethylenediamine component of the original polyamide is replaced with the oligosiloxane diamine.

The copolymer of hydrocarbon-based polyamide and of polyamide-silicone may also be a grafted copolymer comprising a hydrocarbon-based polyamide backbone with pendent oligosiloxane groups.

This may be obtained, for example:

by hydrosilylation of unsaturated bonds in polyamides based on fatty acid dimers;

by silylation of the amide groups of a polyamide; or by silylation of unsaturated polyamides by means of an oxidation, that is to say by oxidizing the unsaturated groups into alcohols or diols, to form hydroxyl groups that are reacted with siloxane carboxylic acids or siloxane alcohols. The olefinic sites of the unsaturated polyamides may also be epoxidized and the epoxy groups may then be reacted with siloxane amines or siloxane alcohols.

The polyorganosiloxane containing polymers used in the composition of the invention are most preferably polymers of the polyorganosiloxane type such as those described in documents U.S. Pat. No. 5,874,069, U.S. Pat. No. 5,919,441, U.S. Pat. No. 6,051,216 and U.S. Pat. No. 5,981,680 and U.S. patent application publication no. 2004/0170586, the entire disclosures of which are hereby incorporated by reference.

According to another embodiment of the invention, the polyorganoxilosane containing polymer is a homopolymer or a copolymer comprising urethane or urea groups.

As previously discussed, the polymer may comprise polyorganosiloxane moieties containing two or more urethane and/or urea groups, either in the backbone of the polymer or on side chains or as pendent groups.

The polymers comprising at least two urethane and/or urea groups in the backbone may be polymers comprising at least one moiety corresponding to the following formula:

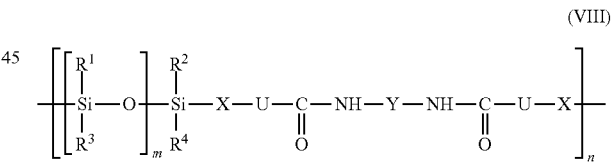

(VIII)

in which $R^1$, $R^2$, $R^3$, $R^4$, X, Y, m and n have the meanings given above for formula (I), and U represents —O— or —NH—, such that:

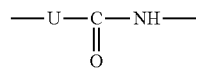

corresponds to a urethane or urea group.

In this formula (VIII), Y may be a linear or branched $C_1$ to $C_{40}$ alkylene group, optionally substituted with a $C_1$ to $C_{15}$ alkyl group or a $C_5$ to $C_{10}$ aryl group. Preferably, a —$(CH_2)_6$— group is used.

Y may also represent a $C_5$ to $C_{12}$ cycloaliphatic or aromatic group that may be substituted with a $C_1$ to $C_{15}$ alkyl group or a $C_5$ to $C_{10}$ aryl group, for example a radical chosen from the methylene-4,4-biscyclohexyl radical, the radical derived from isophorone diisocyanate, 2,4- and 2,6-tolylenes, 1,5-naphthylene, p-phenylene and 4,4'-biphenylenemethane. Generally, it is preferred for Y to represent a linear or branched $C_1$ to $C_{40}$ alkylene radical or a $C_4$ to $C_{12}$ cycloalkylene radical.

Y may also represent a polyurethane or polyurea block corresponding to the condensation of several diisocyanate molecules with one or more molecules of coupling agents of the diol or diamine type. In this case, Y comprises several urethane or urea groups in the alkylene chain.

It may correspond to the formula:

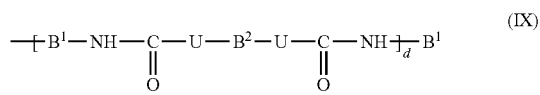

in which $B^1$ is a group chosen from the groups given above for Y, U is —O— or —NH— and $B^2$ is chosen from:

linear or branched $C_1$ to $C_{40}$ alkylene groups, which can optionally bear an ionizable group such as a carboxylic acid or sulphonic acid group, or a neutralizable or quaternizable tertiary amine group, $C_5$ to $C_{12}$ cycloalkylene groups, optionally bearing alkyl substituents, for example one to three methyl or ethyl groups, or alkylene, for example the diol radical: cyclohexanedimethanol, phenylene groups that may optionally bear $C_1$ to $C_3$ alkyl substituents, and groups of formula:

in which T is a hydrocarbon-based trivalent radical possibly containing one or more hetero atoms such as oxygen, sulphur and nitrogen and $R^5$ is a polyorganosiloxane chain or a linear or branched $C_1$ to $C_{50}$ alkyl chain.

T can represent, for example:

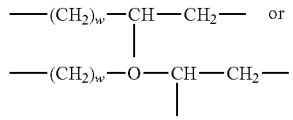

with w being an integer ranging from 1 to 10 and $R^5$ being a polyorganosiloxane chain.

When Y is a linear or branched $C_1$ to $C_{40}$ alkylene group, the —$(CH_2)_2$— and —$(CH_2)_6$— groups are preferred.

In the formula given above for Y, d may be an integer ranging from 0 to 5, preferably from 0 to 3 and more preferably equal to 1 or 2.

Preferably, $B^2$ is a linear or branched $C_1$ to $C_{40}$ alkylene group, in particular —$(CH_2)_2$— or —$(CH_2)_6$— or a group:

with $R^5$ being a polyorganosiloxane chain.

As previously discussed, the polyorganosiloxane containing polymer may be formed from silicone urethane and/or silicone urea moieties of different length and/or constitution, and may be in the form of block or random copolymers.

According to the invention, the silicone may also comprise urethane and/or urea groups no longer in the backbone but as side branches.

In this case, the polymer may comprise at least one moiety of formula:

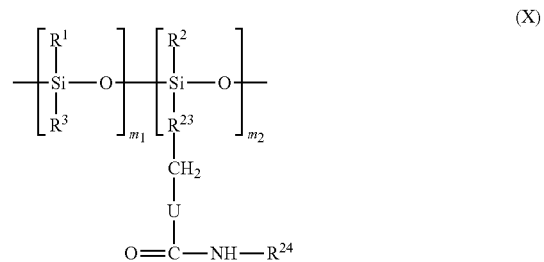

in which $R^1$, $R^2$, $R^3$, $m_1$ and $m_2$ have the meanings given above for formula (I), U represents O or NH, $R^{23}$ represents a $C_1$ to $C_{40}$ alkylene group, optionally comprising one or more hetero atoms chosen from O and N, or a phenylene group, and $R^{24}$ is chosen from linear, branched or cyclic, saturated or unsaturated $C_1$ to $C_{50}$ alkyl groups, and phenyl groups optionally substituted with one to three $C_1$ to $C_3$ alkyl groups.

The polymers comprising at least one moiety of formula (X) contain siloxane units and urea or urethane groups, and they may be used, for example, as gelling agents in the compositions of the invention.

The siloxane polymers may have a single urea or urethane group by branching or may have branches containing two urea or urethane groups, or alternatively they may contain a mixture of branches containing one urea or urethane group and branches containing two urea or urethane groups.

They may be obtained from branched polysiloxanes, comprising one or two amino groups by branching, by reacting these polysiloxanes with monoisocyanates.

As examples of starting polymers of this type containing amino and diamino branches, mention may be made of the polymers corresponding to the following formulae:

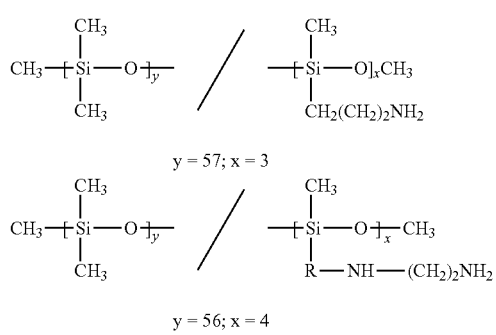

y = 57; x = 3 y = 56; x = 4

In these formulae, the symbol "/" indicates that the segments may be of different lengths and in a random order, and R represents a linear aliphatic group preferably containing 1 to 6 carbon atoms, including 1 to 3 carbon atoms.

Such polymers containing branching may be formed by reacting a siloxane polymer, containing at least three amino groups per polymer molecule, with a compound containing only one monofunctional group (for example an acid, an isocyanate or an isothiocyanate) to react this monofunctional group with one of the amino groups and to form groups capable of establishing hydrogen interactions. The amino groups may be on side chains extending from the main chain of the siloxane polymer, such that the groups capable of establishing hydrogen interactions are formed on these side chains, or alternatively the amino groups may be at the ends of the main chain, such that the groups capable of hydrogen interaction will be end groups of the polymer.

As a procedure for forming a polymer containing siloxane units and groups capable of establishing hydrogen interactions, mention may be made of the reaction of a siloxane diamine and of a diisocyanate in a silicone solvent so as to provide a gel directly. The reaction may be performed in a silicone fluid, the resulting product being dissolved in the silicone fluid, at high temperature, the temperature of the system then being reduced to form the gel.

The polymers that are preferred for incorporation into the compositions according to the present invention are siloxane-urea copolymers that are linear and that contain urea groups as groups capable of establishing hydrogen interactions in the backbone of the polymer.

As an illustration of a polysiloxane ending with four urea groups, mention may be made of the polymer of formula:

in which Ph is a phenyl group and n is a number larger than 0, which includes, at least 1, 2 to 500, 2 to 200, from 1 to 300, in particular from 1 to 100, and all values and subranges there between, for example 50.

This polymer is obtained by reacting the following polysiloxane containing amino groups:

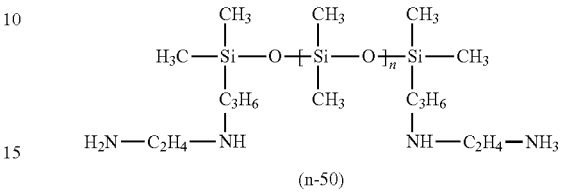

(n-50)

with phenyl isocyanate.

The polymers of formula (VIII) comprising urea or urethane groups in the chain of the silicone polymer may be obtained by reaction between a silicone containing α,ω-$NH_2$ or —OH end groups, of formula:

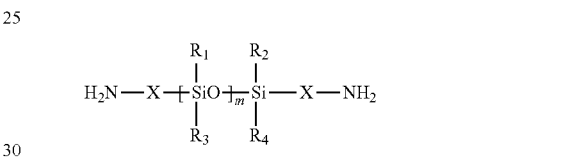

in which m, $R^1$, $R^2$, $R^3$, $R^4$ and X are as defined for formula (I) and a diisocyanate OCN—Y—NCO in which Y has the meaning given in formula (I); and optionally a diol or diamine coupling agent of formula $H_2N$—$B^2$—$NH_2$ or HO—$B^2$—OH, in which $B^2$ is as defined in formula (IX).

According to the stoichiometric proportions between the two reagents, diisocyanate and coupling agent, Y may have the formula (IX) with d equal to 0 or d equal to 1 to 5.

As in the case of the polyamide silicones of formula (II) or (III), it is possible to use in the invention polyurethane or polyurea silicones containing moieties of different length and structure, in particular moieties whose lengths differ by the number of silicone units. In this case, the copolymer may correspond, for example, to the formula:

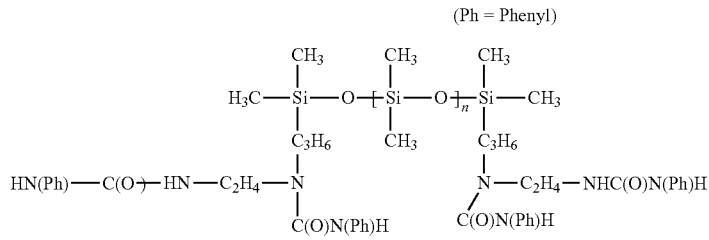

(XI)

(Ph = Phenyl)

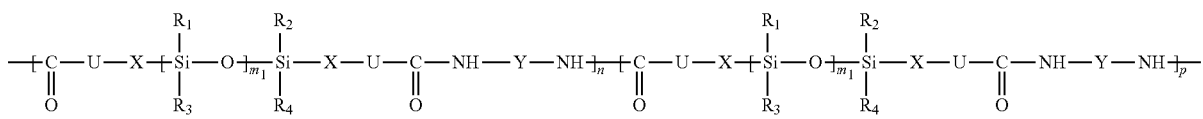

(XII)

in which $R^1$, $R^2$, $R^3$, $R^4$, X, Y and U are as defined for formula (VIII) and $m_1$, $m_2$, n and p are as defined for formula (V).

Branched polyurethane or polyurea silicones may also be obtained using, instead of the diisocyanate OCN—Y—NCO, a triisocyanate of formula:

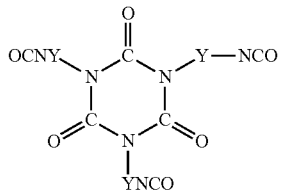

A polyurethane or polyurea silicone containing branches comprising an organosiloxane chain with groups capable of establishing hydrogen interactions is thus obtained. Such a polymer comprises, for example, a moiety corresponding to the formula:

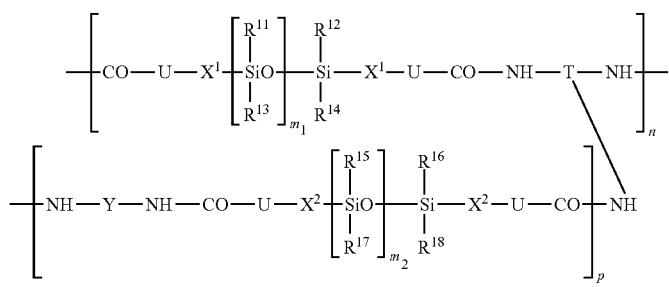

(XIII)

in which $X^1$ and $X^2$, which are identical or different, have the meaning given for X in formula (I), n is as defined in formula (I), Y and T are as defined in formula (I), $R^{11}$ to $R^{18}$ are groups chosen from the same group as $R^1$ to $R^4$, $m_1$ and $m_2$ are as defined above.

As in the case of the polyamides, this copolymer can also comprise polyurethane silicone moieties without branching.

In another embodiment of the invention, the siloxane-based polyureas and polyurethanes that are preferred are:

polymers of formula (VIII) in which m is from 15 to 300, for example, 15 to 100 and all values and subranges there between;

mixtures of two or more polymers in which at least one polymer has a value of m in the range from 15 to 50 and at least one polymer has a value of m in the range from 30 to 300, including all values and subranges there between;

polymers of formula (XII) with $m_1$ chosen in the range from 15 to 50 and $m_2$ chosen in the range from 30 to 500 with the portion corresponding to $m_1$ representing 1% to 99% by weight of the total weight of the polymer and the portion corresponding to $m_2$ representing 1% to 99% by weight of the total weight of the polymer;

mixtures of polymer of formula (VIII) combining
1) 80% to 99% by weight of a polymer in which n is equal to 2 to 10 and in particular 3 to 6, and
2) 1% to 20% of a polymer in which n is in the range from 5 to 500 and in particular from 6 to 100, copolymers comprising two moieties of formula (VIII) in which at least one of the groups Y contains at least one hydroxyl substituent;

polymers of formula (VIII) synthesized with at least one portion of an activated diacid (diacid chloride, dianhydride or diester) instead of the diacid;

polymers of formula (VIII) in which X represents —$(CH_2)_3$— or —$(CH_2)_{10}$—; and polymers of formula (VIII) in which the polymers end with a multifunctional chain chosen from the group consisting of monofunctional amines, monofunctional acids, monofunctional alcohols, including fatty acids, fatty alcohols and fatty amines, such as, for example, octylamine, octanol, stearic acid and stearyl alcohol.

As in the case of the polyamides, copolymers of polyurethane or polyurea silicone and of hydrocarbon-based polyurethane or polyurea may be used in the invention by performing the reaction for synthesizing the polymer in the presence of an α,ω-difunctional block of non-silicone nature, for example a polyester, a polyether or a polyolefin.

As has been seen previously, homopolymers or copolymers of the invention may contain siloxane moieties in the main chain of the polymer and groups capable of establishing hydrogen interactions, either in the main chain of the polymer or at the ends thereof, or on side chains or branches of the main chain. This may correspond to the following five arrangements:

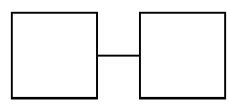

(1)

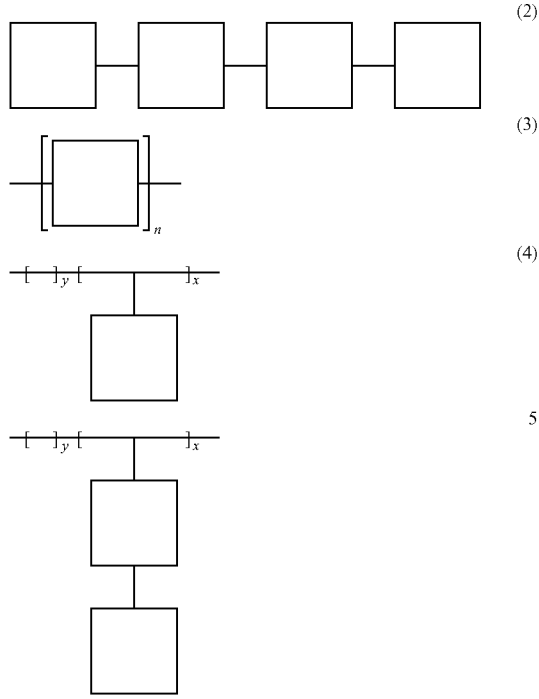

in which the continuous line is the main chain of the siloxane polymer and the squares represent the groups capable of establishing hydrogen interactions.

In case (1), the groups capable of establishing hydrogen interactions are arranged at the ends of the main chain.

In case (2), two groups capable of establishing hydrogen interactions are arranged at each of the ends of the main chain.

In case (3), the groups capable of establishing hydrogen interactions are arranged within the main chain in repeating moieties.

In cases (4) and (5), these are copolymers in which the groups capable of establishing hydrogen interactions are arranged on branches of the main chain of a first series of moieties that are copolymerized with moieties not comprising groups capable of establishing hydrogen interactions. Preferably, the values n, x and y are such that the polymer has the desired properties in terms of an agent for gelling fatty phases, preferably fatty phases based on silicone oil.

As examples of polymers that may be used, mention may be made of the silicone polyamides obtained in accordance with the disclosure in U.S. Pat. No. 5,981,680, the entire disclosure of which is hereby incorporated by reference.

Further examples of polyorganosiloxane containing polymers are set forth in U.S. Pat. Nos. 6,503,632 and 6,569,955, both of which are hereby incorporated by reference in their entirety.

As noted above, the polymers of the present invention can be solid or liquid at room temperature. When solid, the polymers preferably have a softening point from 50 to 130° C. Most preferably, they have a softening point ranging from 65 to 150° C., including from 70° C. to 130° C. This softening point is lower than that of other structuring polymers, which facilitates the use of the polymers that are the subject of the invention, and limits the deteriorations of the liquid fatty phase.

As noted above, the polyorganosiloxane containing polymers of the present invention contain both siloxane units and at least two groups capable of establishing hydrogen interactions such as amide linkages. The siloxane units can provide compatibility with a silicone fluid, if present, (for example with the cyclomethicones), while the groups capable of establishing hydrogen interactions and the spacing and selection of the locations of the amide linkages can facilitate gelation and the formation of cosmetic products.

In one embodiment, the polyorganosiloxane containing polymer of the present invention is present in an amount effective to provide transfer resistant properties, and may also provide at least one of the following properties: pliability, softness, and wearing comfort. In addition, it is preferred that the compositions of the invention exhibit flexibility and/or good adherence on the keratinous substance to which the compositions have been applied. In another preferred embodiment, the compositions of the present invention when applied to the keratinous substance are substantially non-tacky.

In the composition of the present invention, the polyorganosiloxane-containing polymers are preferably present in an amount of from about 1 to about 50 percent by weight, more preferably from 3 to 35 percent by weight and most preferably from 5 to 20 percent by weight of the total weight of the composition.

Volatile Alcohol

According to the present invention, compositions comprising at least one volatile alcohol are provided. The volatile alcohol may be either liner or branched. By "linear volatile alcohol," it is meant a straight chain compound comprising at least one hydroxyl group having a flash point preferably above 0° C., preferably between 0° C. and about 40° C., more preferably between about 10° C. and about 40° C. By "branched volatile alcohol," it is meant a non-straight chain compound comprising at least one hydroxyl group having a flash point preferably above 0° C., preferably between 0° C. and about 40° C., more preferably between about 20° C. and about 40° C.

Preferably, the volatile alcohol has less than 10 carbon atoms, more preferably from 2 to 5 carbon atoms, most preferably from 2 to 4 carbon atoms. Suitable examples include, but are not limited to, ethanol, propanol, butanol, isopropanol, isobutanol, 2-methyl-1-propanol and 3-methyl-1-butanol, and mixtures thereof. In preferred embodiments, at least two volatile alcohols of differing volatility are present in a composition. Thus, for example, a relatively volatile and a relatively non-volatile alcohol can be present in the same composition.

Preferably, the volatile alcohol(s) represent from about 0.1% to about 30% of the total weight of the composition, more preferably from about 0.5% to about 15% of the total weight of the composition, and most preferably from about 1% to about 10%, including all ranges and subranges therebetween.

Also preferably, the ratio of polyorganosiloxane containing polymer to volatile alcohol ranges from about 1:3 to about 70:1. In preferred embodiments, the compositions contain more polyorganosiloxane containing polymer than volatile alcohol, with the ratios of polyorganosiloxane containing polymer to volatile alcohol of about 2:1 to about 35:1 being particularly preferred.

Thickening Agent

According to the present invention, compositions comprising at least one thickening agent are provided. Thickening agents are agents which increase the viscosity of the invention compositions. Such thickening agents can, for example, be chosen from waxes, rheological agents and gelling agents.

Non-limiting examples of acceptable gelling agents include, but are not limited to, gelling agents in polymeric form and gelling agents in mineral form such as, for example, elastomeric polyorganosiloxanes such as those sold or made under the names KSG6 from Shin-Etsu, Trefil E-505C or Trefil E-506C from Dow-Corning, Gransil from Grant Industries (SR-CYC, SR DMF10, SR-DC556) or those marketed in the form of preconstituted gels (KSG15, KSG17, KSG16, KSG18, KSG21 from Shin-Etsu, Gransil SR 5CYC gel, Gransil SR DMF 10 gel, Gransil SR DC556 gel, SF 1204 and JK 113 from General Electric or emulsifying elastomers such as those sold under the names of KSG-210, KSG-30, KSG-31, KSG-32, KSG-33, KSG-40, KSG 41, KSG-42, KSG-43 and KSG-44 from Shin-Etsu, silicone gums, crystalline silicone compounds, non-silicone polyamides, ends of which bear ester or triamides functions, such as compounds described in patents and patent applications U.S. Pat. No. 5,783,657, U.S. Pat. No. 6,268,466, WO 01/95871, WO 00/40216, US 2002/0035237, and EP 1 068 856, the disclosure of which are incorporated herein by reference, polyurethanes, and polymers or copolymers resulting from the polymerization or copolymerization of an ethylenic monomer, in particular use may be made of vinyl, acrylic or methacrylic copolymers which may be block copolymers, such as diblock or triblock copolymers, or even multiblock or starburst or radial copolymers. Such an ethylenic gelling agent may comprise, for example, a styrene block (S), an alkylstyrene block (AS), an ethylene/butylene block (EB), an ethylene/propylene block (EP), a butadiene block (B), an isoprene block (I), an acrylate block (A), a methacrylate block (MA) or a combination of these blocks.

In one embodiment of the present invention, a copolymer comprising at least one styrene block is used as gelling agent or ethylenic rheological agent. A triblock copolymer and in particular those of the polystyrene/polyisoprene or polystyrene/polybutadiene type, such as those sold or made under the name "Luvitol HSB" by BASF and those of the polystyrene/copoly(ethylene-propylene) type or alternatively of the polystyrene/copoly(ethylene/butylene) type, such as those sold or made under the brand name "Kraton" by Shell Chemical Co. or Gelled Permethyl 99A by Penreco, may be used. Styrene-methacrylate copolymers can also be used.

As ethylenical gelling agent which can be used in the composition of the invention, mention may be made, for example, of Kraton G1650 (SEBS), Kraton G1651 (SEBS), Kraton G1652 (SEBS), Kraton G1657X (SEBS), Kraton G1701X (SEP), Kraton G1702X (SEP), Kraton G1726X (SEB), Kraton G1750X (EP) multiarm, Kraton G1765X (EP) multiarm, Kraton D-1101 (SBS), Kraton D-1102 (SBS), Kraton D-1107 (SIS), Gelled Permethyl 99A-750, Gelled Permethyl 99A-753-58 (mixture of starburst block polymer and triblock polymer), Gelled Permethyl 99A-753-59 (mixture of starburst block polymer and triblock polymer), Versagel 5970 and Versagel 5960 from Penreco (mixture of starburst polymer and triblock polymer in isododecane), and OS 129880, OS 129881 and OS 84383 from Lubrizol (styrene-methacrylate copolymer).

Di or triblocks such as polystyrene-copoly(ethylene/propylene) or polystyrene-copoly(ethylene/butylene) such as those described in patent applications WO 98/38981 and US 2002/0055562, the disclosures of which are hereby incorporated by reference, are also included in the present invention.

As modified clays which can be used, mention may be made of hectorites modified with an ammonium chloride of a $C_{10}$ to $C_{22}$ fatty acid, such as hectorite modified with distearyldimethylammonium chloride, also known as quaternium-18 bentonite, such as the products sold or made under the names Bentone 34 by the company Rheox, Claytone XL, Claytone 34 and Claytone 40 sold or made by the company Southern Clay, the modified clays known under the name quaternium-18 benzalkonium bentonites and sold or made under the names Claytone HT, Claytone GR and Claytone PS by the company Southern Clay, the clays modified with stearyldimethylbenzoylammonium chloride, known as steralkonium bentonites, such as the products sold or made under the names Claytone APA and Claytone AF by the company Southern Clay, and Baragel 24 sold or made by the company Rheox.

As other mineral gelling agents which can be used, mention may be made of silica, such as fumed silica. The fumed silica may have a particle size, which may be nanometric to micrometric, for example ranging from about 5 nm to 200 nm.

The fumed silicas may be obtained by high-temperature hydrolysis of a volatile silicon compound in a hydrogen-oxygen flame, producing a finely divided silica. This process makes it possible to obtain hydrophilic silicas that have a large number of silanol groups at their surface. Such hydrophilic silicas are sold or made, for example, under the names "Aerosil 130®", "Aerosil 200®", "Aerosil 255®", "Aerosil 300®" and "Aerosil 380®" by the company Degussa, and "CAB-O-SIL HS-5®", "CAB-O-SIL EH-5®", "CAB-O-SIL LM-130®", "CAB-O-SIL MS-55®" and "CAB-O-SIL M-5®" by the company Cabot.

It is thus possible to chemically modify the surface of the hydrophilic silica by chemical reaction, producing a reduction in the number of silanol groups. The silanol groups can be replaced, for example, with hydrophobic groups: this then gives a hydrophobic silica. The hydrophobic groups may be (a) trimethylsiloxyl groups, which are obtained in particular by treating fumed silica in the presence of hexamethyldisilazane. Silicas thus treated are known as "silica silylate" according to the CTFA (6th edition, 1995). They are sold or made, for example, under the references "Aerosil R812®" by the company Degussa and "CAB-O-SIL TS-530®" by the company Cabot; (b) dimethylsilyloxyl or polydimethylsiloxane groups, which are obtained in particular by treating fumed silica in the presence of polydimethylsiloxane or dimethyldichlorosilane. Silicas thus treated are known as "silica dimethyl silylate" according to the CTFA (6th edition, 1995). They are sold or made, for example, under the references "Aerosil R972®" and "Aerosil R974®" by the company Degussa, and "CAB-O-SIL TS-610®" and "CAB-O-SIL TS-720®" by the company Cabot; and (c) groups derived from reacting fumed silica with silane alkoxides or siloxanes. These treated silicas are, for example, the products sold or made under the reference "Aerosil R805®" by the company Degussa.

According to the invention, hydrophobic silica, such as fumed silica, may be used as lipophilic gelling agent. The use of fumed silica makes it possible to obtain a translucent or even transparent composition, in particular in the form of a stick, which does not exude, in the absence of opacifying particles such as waxes, fillers and pigments (including nacres).

Such thickening agents may also include at least one wax. For the purposes of the present invention, a wax is a lipophilic fatty compound that is solid at room temperature (25° C.) and atmospheric pressure (760 mmHg, i.e. 101 KPa), which undergoes a reversible solid/liquid change of state, having a melting point of greater than 40° C. and further such as greater than 55° C. and which may be up to 200° C. By bringing the wax to its melting point, it is possible to make it miscible with oils and to form a microscopically homogeneous mixture, but on returning the temperature of the mixture to room temperature, recrystallization of the wax in the oils of the mixture is obtained. It is this recrystallization in the mixture which is responsible for the reduction in the gloss of the mixture.

For the purposes of the invention, the waxes are those generally used in cosmetics and dermatology; they are, for example, of natural origin, for instance beeswax, ozokerite, carnauba wax, candelilla wax, ouricury wax, Japan wax, cork fiber wax, sugar cane wax, paraffin wax, lignite wax, microcrystalline waxes, lanolin wax, montan wax, ozokerites and hydrogenated oils such as hydrogenated jojoba oil as well as waxes of synthetic origin, for instance polyethylene waxes derived from the polymerization of ethylene, waxes obtained by Fischer-Tropsch synthesis, fatty acid esters and glycerides that are solid at 40° C., for example, at above 55° C., fatty alcohol waxes such as those sold by Baker Petrolite under the Performacol name (Performacol 350, 425 and 550) including C30-C50 alcohols, silicone waxes such as alkyl- and alkoxy-poly(di)methylsiloxanes and/or poly(di)methyl-siloxane esters that are solid at 40° C., for example, at above 55° C.

According to the invention, the melting point values correspond to the melting peak measured by the "Differential Scanning Calorimetry" method with a temperature rise of 5 or 10° C./min.

The compositions of the present invention may also further comprise liposoluble or dispersible rheological polymers such as, for example, polyalkylenes, in particular polybutene, poly(meth)acrylates, alkylcelluloses with a linear or branched, saturated or unsaturated $C_1$ to $C_8$ alkyl radical, such as ethylcellulose and propylcellulose, silicone polymers that are compatible with the fatty phase, as well as vinylpyrrolidone (VP) copolymers, and mixtures thereof.

Vinylpyrrolidone copolymers, copolymers of a $C_2$ to $C_{30}$, such as $C_3$ to $C_{22}$ alkene, and combinations thereof, can be used. As examples of VP copolymers which can be used in the invention, mention may be made of VP/vinyl acetate, VP/ethyl methacrylate, butylated polyvinylpyrrolidone (PVP), VP/ethyl methacrylate/methacrylic acid, VP/eicosene, VP/hexadecene, VP/triacontene, VP/styrene or VP/acrylic acid/lauryl methacrylate copolymer.

Not only for the staying power properties but also for the feel and consistency properties of the film, the PVP/hexadecene copolymer having an average molecular weight of from 7,000 to 7,500 or alternatively the PVP/eicosene copolymer having an average molecular weight of from 8,000 to 9,000 can be used.

Preferably, the thickening agent(s) represent from about 1% to about 50% of the total weight of the composition, more preferably from about 5% to about 40% of the total weight of the composition, and most preferably from about 7% to about 30%, including all ranges and subranges therebetween.

Volatile Oil

According to particularly preferred embodiments of the present invention, compositions further comprising at least one volatile oil are provided. Preferably, the at least one volatile oil is a silicone volatile oil, a hydrocarbon volatile oil, or a mixture thereof.

According to preferred embodiments, the composition may contain one or more volatile silicone oils. Examples of such volatile silicone oils include linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Specific oils that may be used in the invention include octamethyltrisiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Non-limiting examples of volatile silicone oils are listed in Table 1 below.

TABLE 1

| Compound | Flash Point (° C.) | Viscosity (cSt) |
|---|---|---|
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane(L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |
| PDMS DC 200 (5 cSt) from Dow Corning | 134 | 5 |
| PDMS DC 200 (3St) from Dow Corning | 102 | 3 |

Further, a volatile linear silicone oil may be employed in the compositions of the present invention. Suitable volatile linear silicone oils include those described in U.S. Pat. No. 6,338,839 and WO03/042221, the contents of which are incorporated herein by reference. In one embodiment the volatile linear silicone oil is decamethyltetrasiloxane. In another embodiment, the decamethyltetrasiloxane is further combined with another solvent that is more volatile than decamethyltetrasiloxane.

According to other preferred embodiments, the composition may contain one or more non-silicone volatile oils and may be selected from volatile hydrocarbon oils, volatile esters and volatile ethers. Examples of such volatile non-silicone oils include, but are not limited to, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, isohexadecane, and for example, the oils sold under the trade names of Isopar or Permethyl, the $C_8$ to $C_{16}$ branched esters such as isohexyl or isodecyl neopentanoate and their mixtures. Preferably, the volatile non-silicone oils have a flash point of at least 40° C.

Non-limiting examples of volatile non-silicone volatile oils are given in Table 2 below.

TABLE 2

| Compound | Flash Point (° C.) |
|---|---|
| Isododecane | 43 |
| Isohexadecane | 102 |
| Isodecyl Neopentanoate | 118 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

The volatility of the solvents/oils can be determined using the evaporation speed as set forth in U.S. Pat. No. 6,338,839.

Preferably, the volatile oil(s), when present, represent from about 5% to about 90% of the total weight of the composition, more preferably from about 10% to about 80% of the total weight of the composition, and most preferably from about 20% to about 75%, including all ranges and subranges therebetween.

Also preferably, the volatile oil(s), when present, are present in an amount greater than the amount of volatile alcohol present, preferably in a ratio of at least 2:1 (volatile oil:volatile alcohol), more preferably in a ratio of at least 3:1, more preferably in a ratio of at least 4:1, more preferably in a ratio of at least 5:1, and more preferably in a ratio of at least 6:1.

Coloring Agents

According to particularly preferred embodiments of the present invention, compositions further comprising at least one coloring agent are provided. Preferably, such colored compositions are cosmetic compositions such as, for example, lip compositions (for example, lipstick or liquid lip colors), mascaras, nail polish or foundations.

According to this embodiment, the at least one coloring agent is preferably chosen from pigments, dyes, such as liposoluble dyes, nacreous pigments, and pearling agents.

Representative liposoluble dyes which may be used according to the present invention include Sudan Red, DC Red 17, DC Green 6, R-carotene, soybean oil, Sudan Brown, DC Yellow 11, DC Violet 2, DC Orange 5, annatto, and quinoline yellow. The liposoluble dyes, when present, generally have a concentration ranging up to 20% by weight of the total weight of the composition, such as from 0.0001% to 6%.

The nacreous pigments which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacreous pigments, if present, be present in the composition in a concentration ranging up to 50% by weight of the total weight of the composition, such as from 0.1% to 20%, preferably from 0.1% to 15%, including all ranges and subranges therebetween.

The pigments, which may be used according to the present invention, may be chosen from white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, strontium, calcium, and aluminum.

If present, the pigments may be present in the composition in a concentration ranging up to 50% by weight of the total weight of the composition, such as from 0.5% to 40%, and further such as from 2% to 30%, including all ranges and subranges therebetween. In the case of certain products, the pigments, including nacreous pigments, may, for example, represent up to 50% by weight of the composition.

Film Forming Agents

According to particularly preferred embodiments of the present invention, compositions further comprising at least one film forming agent (film former) are provided. Acceptable film forming agents are known in the art and include, but are not limited to, those disclosed in U.S. patent application publication no. 2004/0170586, the entire contents of which is hereby incorporated by reference. Non-limiting representative examples of such film forming agents include silicone resins such as, for example, MQ resins (for example, trimethylsiloxysilicates) and MK resins (for example, polymethylsilsesquioxanes), silicone esters such as those disclosed in U.S. Pat. Nos. 6,045,782, 5,334,737, and 4,725,658, the disclosures of which are hereby incorporated by reference, polymers comprising a backbone chosen from vinyl polymers, methacrylic polymers, and acrylic polymers and at least one chain chosen from pendant siloxane groups and pendant fluorochemical groups such as those disclosed in U.S. Pat. Nos. 5,209,924, 4,693,935, 4,981,903, 4,981,902, and 4,972,037, and WO 01/32737, the disclosures of which are hereby incorporated by reference, polymers such as those described in U.S. Pat. No. 5,468,477, the disclosure of which is hereby incorporated by reference (a non-limiting example of such polymers is poly(dimethylsiloxane)-g-poly(isobutyl methacrylate), which is commercially available from 3M Company under the tradename VS 70 IBM).

According to preferred embodiments, the film former, when present, is present in the composition in an amount ranging from 0.1% to 30% by weight relative to the total weight of the composition. Preferably, the film former is present in an amount ranging from 0.5% to 25% by weight relative to the total weight of the composition, and more preferably from 2% to 20%, including all ranges and subranges therebetween. One of ordinary skill in the art will recognize that the film former of the present invention may be commercially available, and may come from suppliers in the form of a dilute solution. The amounts of the film former disclosed herein therefore reflect the weight percent of active material.

According to particularly preferred embodiments, when a film forming agent is present, the combined amount of polyorganosiloxane containing polymer(s) and the film forming agents is 20-60% by weight of the entire weight of the composition. In particularly preferred embodiments, the polyorganosiloxane containing polymer is a silicone-polyamide copolymer and the film forming agent is a silicone resin, in particular trimethylsiloxysilicate.

According to preferred embodiments of the present invention, the compositions of the present invention are anhydrous. By "anhydrous," it is meant that the composition contains substantially no water (that is, less than about 0.5% by weight of the composition of water).

According to other preferred embodiments, the compositions of the present invention further comprise water. In this embodiment, water is preferably present in an amount ranging from about 0.6 to about 70%, preferably from about 3.0 to 60%, and more preferably from about 5 to about 50% relative to the total weight of the composition. Preferably, such water-containing cosmetic compositions are lip compositions (for example, lipstick or liquid lip colors), foundations or mascaras, and are emulsions or dispersions.

Additional Additives

The composition of the invention can also comprise any additive usually used in the field under consideration. For example, dispersants such as poly(12-hydroxystearic acid), antioxidants, essential oils, sunscreens, preserving agents, fragrances, fillers, neutralizing agents, cosmetic and dermatological active agents such as, for example, emollients, moisturizers, vitamins, essential fatty acids, surfactants, pasty compounds and mixtures thereof can be added. A non-exhaustive listing of such ingredients can be found in U.S. patent application publication no. 2004/0170586, the entire contents of which is hereby incorporated by reference. Further examples of suitable additional components can be found in the other references which have been incorporated by reference in this application. Still further examples of such additional ingredients may be found in the *International Cosmetic Ingredient Dictionary and Handbook* ($9^{th}$ ed. 2002).

A person skilled in the art will take care to select the optional additional additives and/or the amount thereof such that the advantageous properties of the composition according to the invention are not, or are not substantially, adversely affected by the envisaged addition.

These substances may be selected variously by the person skilled in the art in order to prepare a composition which has the desired properties, for example, consistency or texture.

These additives may be present in the composition in a proportion from 0% to 99% (such as from 0.01% to 90%) relative to the total weight of the composition and further such as from 0.1% to 50% (if present), including all ranges and subranges therebetween.

According to a particularly preferred embodiment of the present invention, the invention compositions contain less than 25% by weight with respect to the total weight of the composition of particulate matter (that is, particulate matter such as pigments and fillers which do not dissolve and/or are not soluble in the invention compositions), more preferably less than 20%, and most preferably less than 15%.

Needless to say, the composition of the invention should be cosmetically or dermatologically acceptable, i.e., it should contain a non-toxic physiologically acceptable medium and should be able to be applied to the eyelashes of human beings.

Non-limiting examples of such additional components include non-volatile oils such as silicone oils (for example, dimethicone, phenyl trimethicone, trimethyl pentaphenyl trisiloxane, etc) or hydrocarbon oils (for example, esters). In one embodiment of the present invention, the compositions of the present invention are substantially free of silicone oils (i.e., contain less than about 0.1% silicone oils). In another embodiment, the compositions are substantially free of non-silicone oils (i.e., contain less than about 0.1% non-silicone oils). In another embodiment, the compositions are substantially free of non-volatile oils (i.e., contain less than about 0.1% non-volatile oils).

The compositions according to the present disclosure may also comprise at least one fatty compound that is pasty at room temperature. As used herein, the expression "pasty fatty substance," is understood to mean fatty substances with a melting point ranging from 20° C. to 55° C., for instance from 25.° C. to 45° C., and/or a viscosity at 40° C. ranging from 0.1 Pa·s to 40 Pa·s (1 to 400 poises), such as from 0.5 Pa·s to 25 Pa·s, measured using a Contraves TV or Rheomat 80 viscometer, equipped with a spindle rotating at 60 Hz. A person skilled in the art can select the spindle for measuring the viscosity from the spindles MS-r3 and MS-r4, on the basis of general knowledge, so as to be able to carry out the measurement of the pasty compound tested.

These fatty substances may be, for example, hydrocarbon-based compounds, optionally of polymeric type; they can also be chosen from silicone compounds; they may also be in the form of a mixture of hydrocarbon-based compounds and/or silicone compounds. In the case of a mixture of different pasty fatty substances, the hydrocarbon-based pasty compounds (comprising mainly hydrogen and carbon atoms and optionally ester groups) may be, for instance, used in major proportion.

Among the pasty compounds which may be used in the compositions according to the present disclosure, non-limiting mention may be made of lanolins and lanolin derivatives such as acetylated lanolins or oxypropylenated lanolins or isopropyl lanolate, and mixtures thereof. It is also possible to use esters of fatty acids or of fatty alcohols, for example, those comprising from 20 to 65 carbon atoms such as triisostearyl or cetyl citrate; arachidyl propionate; polyvinyl laurate; BIS-DIGLYCERYL POLYACYLADIPATE-2; cholesterol esters, such as triglycerides of plant origin, such as hydrogenated plant oils, viscous polyesters such as poly(12-hydroxystearic acid), and mixtures thereof. Further non-limiting mention may also be made of pasty silicone fatty substances such as polydimethylsiloxanes (PDMSs) comprising pendent chains of the alkyl or alkoxy type comprising from 8 to 24 carbon atoms, and such as stearyldimethicones, for instance, those sold by Dow Corning under the trade names DC2503 and DC25514, and mixtures thereof.

According to preferred embodiments of the present invention, methods of treating, caring for and/or making up keratinous material such as skin, lips, hair and mucous membranes by applying compositions of the present invention to the keratinous material in an amount sufficient to treat, care for and/or make up the keratinous material are provided. Preferably, "making up" the keratin material includes applying at least one coloring agent to the keratin material in an amount sufficient to provide color to the keratin material.

According to other preferred embodiments, methods of covering or hiding defects associated with keratinous material such as imperfections or discolorations by applying compositions of the present invention to the keratinous material in an amount sufficient to cover or hide such defects are provided.

According to yet other preferred embodiments, methods of enhancing the appearance of keratinous material by applying compositions of the present invention to the keratinous material in an amount sufficient to enhance the appearance of the keratinous material are provided.

In accordance with the three preceding preferred embodiments, the compositions of the present invention comprising at least one polyorganosiloxane containing polymer, preferably a polysilicone-polyamide copolymer, at least one volatile alcohol and at least one thickening agent are applied topically to the desired area of the skin in an amount sufficient to treat, care for and/or make up the keratinous material, to cover or hide defects associated with keratinous material, skin imperfections or discolorations, or to enhance the appearance of keratinous material. The compositions may be applied to the desired area as needed, preferably once or twice daily, more preferably once daily and then preferably allowed to dry before subjecting to contact such as with clothing or other objects (for example, a glass or a topcoat). Preferably, the composition is allowed to dry for about 5 minutes or less, more preferably for about 2 minutes or less. The composition is preferably applied to the desired area that is dry or has been dried prior to application, or to which a basecoat has been previously applied. Most preferably, the composition further comprises at least one coloring agent, at least one film forming agent and/or at least one volatile oil.

According to a preferred embodiment of the present invention, compositions having improved cosmetic properties such as, for example, improved feel upon application (for example, deposit), long wear, transfer resistance or waterproof properties are provided. The improved properties may also be chosen from improved flexibility, wearability, drying time or retention as well as reduced tackiness or migration over time.

The present invention also envisages kits and/or prepackaged materials suitable for consumer use containing one or more compositions according to the description herein. The packaging and application device for any subject of the invention may be chosen and manufactured by persons skilled in the art on the basis of their general knowledge, and adapted according to the nature of the composition to be packaged. Indeed, the type of device to be used can be in particular linked to the consistency of the composition, in particular to its viscosity; it can also depend on the nature of the constituents present in the composition, such as the presence of volatile compounds.

According to particularly preferred embodiments, kits of the present invention comprise (a) a composition comprising at least one polyorganosiloxane containing polymer, at least one thickening agent and at least one volatile alcohol; and (b) a basecoat and/or topcoat composition.

In accordance with this embodiment, the composition (a) corresponds to the invention compositions described above, while the composition (b) is/are composition(s) applied before and/or after the invention composition, typically known in the art as basecoats (applied before) and topcoats (applied after). No particular requirements exist for the basecoats and topcoats which can be used in conjunction with the compositions of the present invention and, thus, such basecoats and topcoats can contain ingredients such as those discussed above. Preferably, however, such basecoats and topcoats should not have overly deleterious effects on the properties of the invention compositions (for example, the basecoats or topcoats should not unacceptably affect the transfer-resistance properties of the invention compositions).

For example, in accordance with particularly preferred embodiments of the present invention, kits comprising (a) a basecoat composition comprising at least one polyorganosiloxane containing polymer, at least one thickening agent and at least one volatile alcohol; and (b) a topcoat composition comprising a non-volatile solvent are provided. According to particularly preferred embodiments, such a basecoat composition further comprises at least one volatile oil, preferably a volatile hydrocarbon oil, and such a topcoat composition comprises at least one non-volatile silicone oil. According to particularly preferred embodiments, such kits are used to make up skin or lips, particularly lips.

In a preferred embodiment, kits of the present invention comprise two or more solid compositions. For example, the kit may comprise (a) a solid composition comprising at least one polyorganosiloxane containing polymer, at least one thickening agent and at least one volatile alcohol; and (b) a solid basecoat and/or topcoat composition.

In a particularly preferred embodiment, kits of the present invention comprise (a) a solid composition comprising at least one silicone-polyamide copolymer, at least one coloring agent, at least one thickening agent, and at least one volatile alcohol; and (b) a solid topcoat composition comprising at least one oil and/or at least one wax.

According to yet other embodiments of the present invention, methods of making a non-liquid composition, preferably a solid composition, comprising mixing together at least one polyorganosiloxane containing polymer, preferably a silicone-polyamide copolymer, at least one thickening agent, and at least one volatile alcohol and at least one thickening agent to form a non-liquid composition are provided. According to such preferred embodiments, the at least one volatile alcohol enables more rapid dissolution of the polyorganosiloxane containing polymer during the preparation of the non-liquid composition. According to particularly preferred embodiments, such more rapid dissolution enables lower temperatures/lesser amounts of time to be used during the preparation of the non-liquid composition Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLE 1

Solid Basecoat (Lipstick or Foundation)

| INCI name | Concentration |
| --- | --- |
| LAUROYL LYSINE | 0.90 |
| IRON OXIDES | 1.7830 |
| IRON OXIDES | 0.0310 |
| TITANIUM DIOXIDE | 1.6650 |
| DISTEARDIMONIUM HECTORITE (and) PROPYLENE CARBONATE | 8.68 |
| FRAGRANCE | 0.20 |
| MICA | 4.0210 |
| POLYETHYLENE WAX | 8.91 |
| TRIMETHYLSILOXYSILICATE | 21.55 |
| NYLON-611/DIMETHICONE COPOLYMER | 13.90 |
| ISOPROPYL ALCOHOL | 5 |
| ISODODECANE | 28.24 |
| C30-50 ALCOHOLS | 5.12 |

EXAMPLE 2

Solid Topcoat

| USA INCI name | Concentration |
| --- | --- |
| TRIMETHYL PENTAPHENYL TRISILOXANE (DOW CORNING PH-1555 HRI COSMETIC FLUID) | 90.0 |
| OZOKERITE | 5.5 |
| BEESWAX | 4.5 |
| Total | 100.0 |

EXAMPLE 3

Solid Topcoat

| INCI name | Concentration |
| --- | --- |
| TRIMETHYL PENTAPHENYL TRISILOXANE (DOW CORNING PH-1555 HRI COSMETIC FLUID) | 92.50 |
| OZOKERITE | 3.25 |
| BEESWAX | 4.25 |
| Total | 100.00 |

EXAMPLE 4

Solid Topcoat

| USA INCI name | Concentration |
|---|---|
| TRIMETHYL PENTAPHENYL TRISILOXANE (DOW CORNING PH-1555 HRI COSMETIC FLUID) | 95.0 |
| OZOKERITE | 2.0 |
| BEESWAX | 3.0 |
| Total: | 100.0 |

What is claimed is:

1. A composition comprising at least one silicone-polyamide copolymer, a C3 volatile alcohol and at least one thickening agent.

2. The composition of claim 1, further comprising at least one film forming agent.

3. The composition of claim 2, wherein the film forming agent is trimethylsiloxysilicate.

4. The composition of claim 1, further comprising at least one coloring agent.

5. The composition of claim 1, further comprising at least one volatile oil.

6. The composition of claim 1, wherein the composition is solid.

7. The composition of claim 6, further comprising at least one film forming agent.

8. The composition of claim 6, further comprising at least one coloring agent in an amount sufficient to provide color to a keratin material upon application to the keratin material.

9. The composition of claim 6, wherein the thickening agent is a wax.

10. The composition of claim 5, wherein the volatile oil is a volatile hydrocarbon oil.

11. The composition of claim 1, wherein the C3 volatile alcohol is a branched volatile alcohol.

12. The composition of claim 11, wherein the branched C3 volatile alcohol is isopropanol.

13. The composition of claim 1, wherein the composition is anhydrous.

14. The composition of claim 1, wherein the silicone-polyamide copolymer is a nylon 611/dimethicone copolymer.

15. A kit comprising (a) a basecoat composition comprising at least one silicone-polyamide copolymer, a C3 volatile alcohol, at least one thickening agent and at least one coloring agent; and (b) a topcoat composition comprising at least one oil.

16. The composition of claim 1, wherein the silicone-polyamide copolymer to volatile alcohol ratio ranges from 2:1 to 35:1.

17. A method for applying color to skin or lips comprising applying the composition according to claim 1 to skin or lips in an amount sufficient to color the skin or lips.

18. The composition of claim 1, wherein the composition is free of antiperspirant.

19. The composition of claim 1, wherein the composition is not in the form of a deodorant.

* * * * *